(12) United States Patent
Dempster et al.

(10) Patent No.: US 7,022,087 B2
(45) Date of Patent: Apr. 4, 2006

(54) AIR CIRCULATION APPARATUS AND METHODS FOR PLETHYSMOGRAPHIC MEASUREMENT CHAMBERS

(75) Inventors: Philip T. Dempster, Concord, CA (US); Michael V. Homer, Oakland, CA (US); Mark Lowe, Danville, CA (US); Alessandro Urlando, Sacramento, CA (US)

(73) Assignee: Life Measurement, Inc., Concord, CA (US)

( * ) Notice: Subject to any disclaimer, the term of this patent is extended or adjusted under 35 U.S.C. 154(b) by 113 days.

(21) Appl. No.: 10/402,225

(22) Filed: Mar. 26, 2003

(65) Prior Publication Data

US 2004/0193074 A1    Sep. 30, 2004

(51) Int. Cl.
*A61B 5/103*  (2006.01)

(52) U.S. Cl. .......................... 600/587; 73/149
(58) Field of Classification Search ................ 600/300, 600/301, 529, 533, 587, 21, 22; 119/417, 119/420; 128/200.24; 73/149, 433, 865.6
See application file for complete search history.

(56) References Cited

U.S. PATENT DOCUMENTS

| | | | |
|---|---|---|---|
| 3,511,237 A * | 5/1970 | Jaeger ........................ 600/533 |
| 4,184,371 A | 1/1980 | Brachet | |
| 4,369,652 A | 1/1983 | Gundlach | |
| 4,406,289 A | 9/1983 | Wesseling et al. | |
| 4,539,997 A | 9/1985 | Wesseling et al. | |
| 4,587,967 A * | 5/1986 | Chu et al. .............. 128/204.21 |
| 4,640,130 A | 2/1987 | Sheng et al. | |
| 4,671,297 A * | 6/1987 | Schulze, Jr. ................ 600/529 |
| 4,676,253 A | 6/1987 | Newman et al. | |
| 4,888,718 A | 12/1989 | Furuse | |
| 4,972,842 A * | 11/1990 | Korten et al. ............... 600/529 |
| 5,105,825 A | 4/1992 | Dempster | |
| 5,379,777 A | 1/1995 | Lomask | |
| 5,450,750 A | 9/1995 | Abler | |
| 5,620,005 A | 4/1997 | Ganshorn | |
| 5,632,270 A * | 5/1997 | O'Mahony et al. ..... 128/204.24 |
| 5,881,724 A * | 3/1999 | Graetz et al. .......... 128/204.23 |
| 6,158,430 A * | 12/2000 | Pfeiffer et al. ......... 128/202.27 |
| 6,702,661 B1 * | 3/2004 | Clifton et al. .............. 454/184 |
| 6,702,764 B1 * | 3/2004 | Dempster et al. ........... 600/587 |
| 6,778,926 B1 * | 8/2004 | Dempster .................... 702/97 |

OTHER PUBLICATIONS

Bailey et al., "Test-Retest Reliability of Body Fat Percentage Results Using Dual Energy X-Ray Absorptiometry and the BOD POD," *Presented at the American College of Sports Medicine 48th Annual Meeting, May 30-Jun. 2, 2001 in Baltimore, Maryland* (abstract only).

(Continued)

*Primary Examiner*—Charles Marmor
(74) *Attorney, Agent, or Firm*—Fish & Neave IP Group Ropes & Gray LLP; Mark D. Rowland; Chi-Hsin Chang

(57) ABSTRACT

Apparatus and methods relating to circulation of air within a plethysmographic measurement chamber are provided. An air circulation system, comprised of one or more pumps, is coupled to a plethysmographic measurement chamber using one or more inlet and exhaust tubes. The air circulation system renews the air within the measurement chamber using ambient air, or air derived from a controlled temperature environment.

51 Claims, 4 Drawing Sheets

OTHER PUBLICATIONS

Biaggi et al., "Comparison of Air-Displacement Plethysmography with Hydrostatic Weighing and Bioelectrical Impedance Analysis for the Assessment of Body Composition in Healthy Adults 1-3," *American Journal of Clinical Nutrition* vol. 69: pp. 898-903 (1999).

Dempster et al., "A New Air Displacement Method for the Determination of Human Body Composition," *Med Sci Sports Exerc.* 1995 Dec.; 27(12): 1692-7.

Dewit et al., "Whole Body Air Displacement Plethysmography Compa5red with Hydrodensitometry for Body Composition Analysys," *Archives of Disease in Childhood* vol. 82 No. 2: pp. 159-164 (Feb. 2000).

Ellis et al., "Can Air-Displacement Plethysmography Replace Hydrodensitometry for Body Composition Analysis in Children and Adults," *Presented at Experimental Biology 2001 in Orlando, Florida* (abstract only).

Fields et al., "Body Composition Techniques and the Four-Comparment Model in Children," *Journal of Applied Physiology* vol. 89: pp. 613-620 (2000).

Gundlach et al., "The Plethysmometric Measurement of Total Body Volume," *Human Biology* vol. 58 No. 5: pp. 783-799 (Oct. 1986).

Higgins et al., "Effect of Scalp and Facial Hair on Air Displacement Plethysmography Estimates of Percentage Body Fat," *Obes Res* May 2001; 9(5): 326-330.

http://academic.wsc.edu/hpls/glass_s/onlineped103/chapter4.htm, "What Fat is Linked to; Slides 4, 13-17, 20, 21, 23, 26, 28, 30" (Dec. 26, 2001).

http://www.geocities.com/HotSprings/5484/thesis/thesis2.htm, "Chapter II: Review of Literature on Body Composition" (Dec. 26, 2001).

http://hnrc.tufts.edu, "Laboratories and Programs: Body Composition Research Program" (Dec. 26, 2001).

http://www.nal.usda.gov/ttic/tektran/data/000009/27/0000092775.html, "Tektran Agriculture Research Service: Body Composition in Children and Adults by Air Displacement Plethysmography" (Dec. 26, 2001).

http://www.coe.uh.edu/~bsekula/pep6301/Ch.%2027%20Mkk.htm, "Body Composition Assessment" (Dec. 26, 2001).

http://odp.od.nih.gov/consensus/ta/015/015_intro.htm, "State of the Science Statements NIH Consensus Development Program: Bioelectrical Impedance Analysis in Body Composition Measurement—Dec. 12-14, 1994: 15. Bioelectrical Impedance Analysis in Body Composition Measurement" (Dec. 26, 2001).

http://brc.montana.edu/olympics/physiology/pb03.html, "Physiology & Psychology Performance Benchmarks: Body Composition and Body Mass" (Dec. 26, 2001).

LeCheminant et al., "Differences in Body Fat Percentage Measured Using Dual Energy X-Ray Absorptiometry and the BOD POD in 100 Women," *Presented at the American College of Sports Medicine 48th Annual Meeting, May 30-Jun. 2, 2001 in Baltimore, Maryland* (abstract only).

Lockner et al, "Comparison of Air-Displacement Plethysmography, Hydrodensitometry, and Dual X-ray Absorptiometry for Assessing Body Composition of Children 10 to 18 Years of Age," *Annals of the New York Academy of Sciences* vol. 904—*In Vivo Body Composition Studies*: pp. 72-78 (May 2000).

Maddalozzo et al., "Concurrent Validity of the BOD POD and Dual Energy X-Ray Absorptiometry Techniques for Assessing the Body Fat Percentage in Young Women," *Presented at the American College of Sports Medicine 48th Annual Meeting, May 30-Jun. 2, 2001 in Baltimore, Maryland* (abstract only).

McCrory et al., "Evaluation of a New Air Displacement Plethysmograph for Measuring Human Body Composition," *Med Sci Sports Exerc.* Dec. 1995; 27(12): 1686-91.

McCrory et al., "Comparison of Methods for Measuring Body Composition Responses to Progressive Resistance Training in Hispanic Elders with Type 2 Diabetes," *Presented at Experimental Biology 2001 in Orlando, Florida* (abstract only).

Miyatake et al., "A New Air Displacement Plethysmograph for the Determination of Japanese Body Composition," *Diabetes Obes Metab* Nov. 1999; 1(6): 347-51.

Nicholson et al., "Estimation of Body Fatness by Air Displacement Plethysmography in African American and White Children," *Pediatric Research* vol. 50 No. 4: pp. 467-473 (2001).

Nunez et al., "Body Composition in Children and Adults by Air Displacement Plethysmography," *Eur J Clin Nutr.* May 1999; 53(5): 382-7.

Wagner et al., "Techniques of Body Composition Assessment: A Review of Laboratory and Field Methods," *Research Quarterly for Exercise and Sport:* pp. 135-149 (Jun. 1999).

Yee et al., "Calibration and Validation of an Air-Displacement Plethysmography Method for Estimating Percentage Body Fat in an Elderly Population: A Comparison among Compartmental Models 1-3," *American Journal of Clinical Nutrition* vol. 74: pp. 637-642 (2001).

\* cited by examiner

AIR CIRCULATION APPARATUS AND METHODS FOR PLETHYSMOGRAPHIC MEASUREMENT CHAMBERS

FIELD OF THE INVENTION

This invention relates generally to apparatus and methods for providing accurate measurement of human body composition using a plethysmographic measurement chamber. More specifically, the present inventions relate to apparatus and methods for plethysmographic measurement of human subjects in which air within a plethysmographic measurement chamber is circulated and renewed with air from outside the chamber.

BACKGROUND OF THE INVENTION

The assessment of body composition, including measurement of fat and fat-free mass, provides physicians with important information regarding physical status. Excess body fat has been associated with a variety of disease processes, such as cardiovascular disease, diabetes, hypertension, hyperlipidemia, kidney disease, and musculoskeletal disorders. Low levels of fat free mass have been found to be critically adverse to the health of certain at-risk populations, such as infants, the obese, and the elderly.

Similarly, body composition has been shown to be useful as a diagnostic measurement for the assessment of physical status. Disturbances in health and growth, regardless of origin, almost always affect body composition in newborns and infants. For example, for very low birth weight infants, body composition and variation in body composition are relevant both in determining infant energy needs and in evaluation of health progression and physical development.

A variety of methods are currently used in the assessment of body composition. One common method is a skin fold measurement, typically performed using calipers that compress the skin at certain points on the body. While non-invasive, this method suffers from poor accuracy on account of variations in fat patterning, misapplication of population specific prediction equations, improper site identification for compressing the skin, poor fold grasping, and the necessity for significant technician training to administer the test properly.

Another method employed is bioelectric impedance analysis ("BIA"). Bioelectric impedance measurements rely on the fact that the body contains intracellular and extracellular fluids that conduct electricity. In particular, BIA involves passing a high frequency electric current through the subject's body, determining the subjects' measured impedance value, and calculating body composition based on the subject's measured impedance and known impedance values for human muscle tissue. However, this method can be greatly affected by the state of hydration of the subject, and variations in temperature of both the subject and the surrounding environment. Moreover, BIA has not been successfully applied with infant subjects.

The most common method used when precision body composition measurements are required is hydrostatic weighing. This method is based upon the application of Archimedes principle, and requires weighing the subject on land, repeated weighing under water, and an estimation of air present in the lungs of the subject using gas dilution techniques. However, hydrodensitometry is time consuming, typically unpleasant for the subjects, requires both significant subject participation and considerable technician training and, due to the necessary facilities for implementation, is unsuitable for clinical practice. Further, the application of hydrodensitometry to infant, elderly, and disabled populations is precluded by the above concerns.

One technique offering particular promise in performing body mass measurement is the use of air displacement plethysmography. Air displacement plethysmography determines the volume of a subject to be measured by measuring the volume of air displaced by the subject in an enclosed chamber. Volume of air in the chamber is calculated through application of Boyle's Law and/or Poisson's Law to conditions within the chamber. More particularly, in the most prevalent method of air displacement plethysmography used for measuring human body composition (such as disclosed in U.S. Pat. No. 4,369,652, issued to Gundlach, and U.S. Pat. No. 5,105,825, issued to Dempster), volume perturbations of a fixed frequency of oscillation are induced within a measurement chamber, which perturbations lead to pressure fluctuations within the chamber. The amplitude of the pressure fluctuations is determined, and used to calculate the volume of air within the chamber using Boyle's Law (defining the relationship of pressure and volume under isothermal conditions) or Poisson's law (defining the relationship of pressure and volume under adiabatic conditions). Body volume is then calculated indirectly by subtracting the volume of air remaining inside the chamber when the subject is inside from the volume of air in the chamber when it is empty.

Once the volume of the subject is known, body composition can be calculated based on the measured subject volume, weight of the subject, and subject surface area (which, for human subjects, is a function of subject weight and subject height), using known formulas defining the relationship between density and human fat mass. For example, Siri's equation defines fat mass as Percent Fat Mass=((4.95/Density)−4.5)*100)

where Density is defined as subject weight/subject volume.

Similarly, Brozek's equation defines fat mass as

Percent Fat mass=((4.57/Density)−4.142)*100)

where Density is defined as subject weight/subject volume.

In contrast to hydrodensitometry, air displacement plethysmographic methods generally do not cause anxiety or discomfort in the subject, and due to the ease and non-invasiveness of the technique, can be applied to subjects for whom hydrodensitometry is impractical. For example, co-pending U.S. patent application Ser. No. 10/036,139, issued as U.S. Pat. No. 6,702,764, entitled Apparatus And Methods For Plethysmographic Measurement of Infant Body Composition, applied for by Philip Dempster, and filed on Dec. 31, 2001, describes apparatus and methods for plethysmographic measurement of body composition of infant subjects.

However, plethysmographic systems require very accurate measurements of volume to yield valid body composition results. In particular, plethysmographic measurement of infant body composition requires even more accurate measurement of volume given the higher metabolic activity of infant subjects as a proportion of body size, and the longer measurement periods required for infants on account of larger breathing artifacts. Due to this required accuracy of volume measurement, current plethysmographic measurement systems, while effective at measuring the volume of inanimate objects, have suffered from secondary effects that limit the accuracy of those systems with human subjects. For example, accumulation of water vapor and $CO_2$ in the measurement chamber can significantly affect results on account of the differing adiabatic compression properties of triatomic gasses (such as $CO_2$ and $H_2O$) and diatomic gasses (such as $O_2$ and $N_2$). Similarly, variations in chamber temperature due to body heat produced by a test subject may also affect the accuracy of volume measurement.

Further, the composition of air within the measurement chamber has an effect on the comfort and safety of the test subject. Specifically, accumulation of $CO_2$ beyond certain levels may adversely affect the infant subject. Thus, current plethysmographic systems that do not account for accumulation of triatomic gasses tend to be less suitable for determining infant body composition.

In view of the foregoing, it would be desirable to provide a plethysmographic measurement chamber that prevented the accumulation of water vapor and $CO_2$ in the chamber, resulting in improved accuracy of body composition measurement.

It would further be desirable to provide a plethysmographic measurement chamber and air circulation system that addressed variations in chamber temperature on account of body heat produced by the test subject.

It would further be desirable to provide a plethysmographic measurement chamber and air circulation system that maintained a safe and comfortable air composition for infant test subjects.

SUMMARY OF THE INVENTION

In view of the foregoing, it is an object of the present invention to provide a plethysmographic measurement chamber that prevents the accumulation of water vapor and $CO_2$ in the chamber.

It is another object of the present invention to provide a plethysmographic measurement chamber that addressed variations in chamber temperature on account of body heat produced by the test subject.

It is another object of the present invention to provide a plethysmographic measurement chamber and air circulation system that maintains a safe and comfortable air composition for infant test subjects.

These and other objects of the present invention are accomplished by providing systems and methods for circulating and renewing air within a plethysmographic measurement chamber, while maintaining the acoustic properties of the measurement chamber at the perturbation frequency used to conduct volume measurements.

The present invention generally consists of a plethysmographic measurement system that includes an air circulation system. The air circulation system comprises a pump assembly of one or more pumps coupled to the measurement chamber via one or more inlet tubes and one or more exhaust tubes. The lengths of the inlet tube(s) and exhaust tube(s) are selected such that the acoustic properties of the measurement chamber are not affected by the air circulation system.

In one embodiment of the present invention, the source of air for the air circulation system is a controlled temperature environment, such that chamber temperature can be maintained relatively constant in spite of body heat produced by the test subject.

In another embodiment of the present invention, the inlet tube and exhaust tube further comprise multiple parallel tubes to provide for quieter, laminar flow within the tubes.

In another embodiment of the present invention, a single inlet tube and a single exhaust tube are coupled between the pump assembly and an inlet manifold and exhaust manifold, respectively. The inlet manifold and exhaust manifold are then coupled to the chamber via multiple parallel tubes, providing for less flow resistance than full lengths of multiple parallel tubes, while still attenuating noise generated by turbulent flow.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
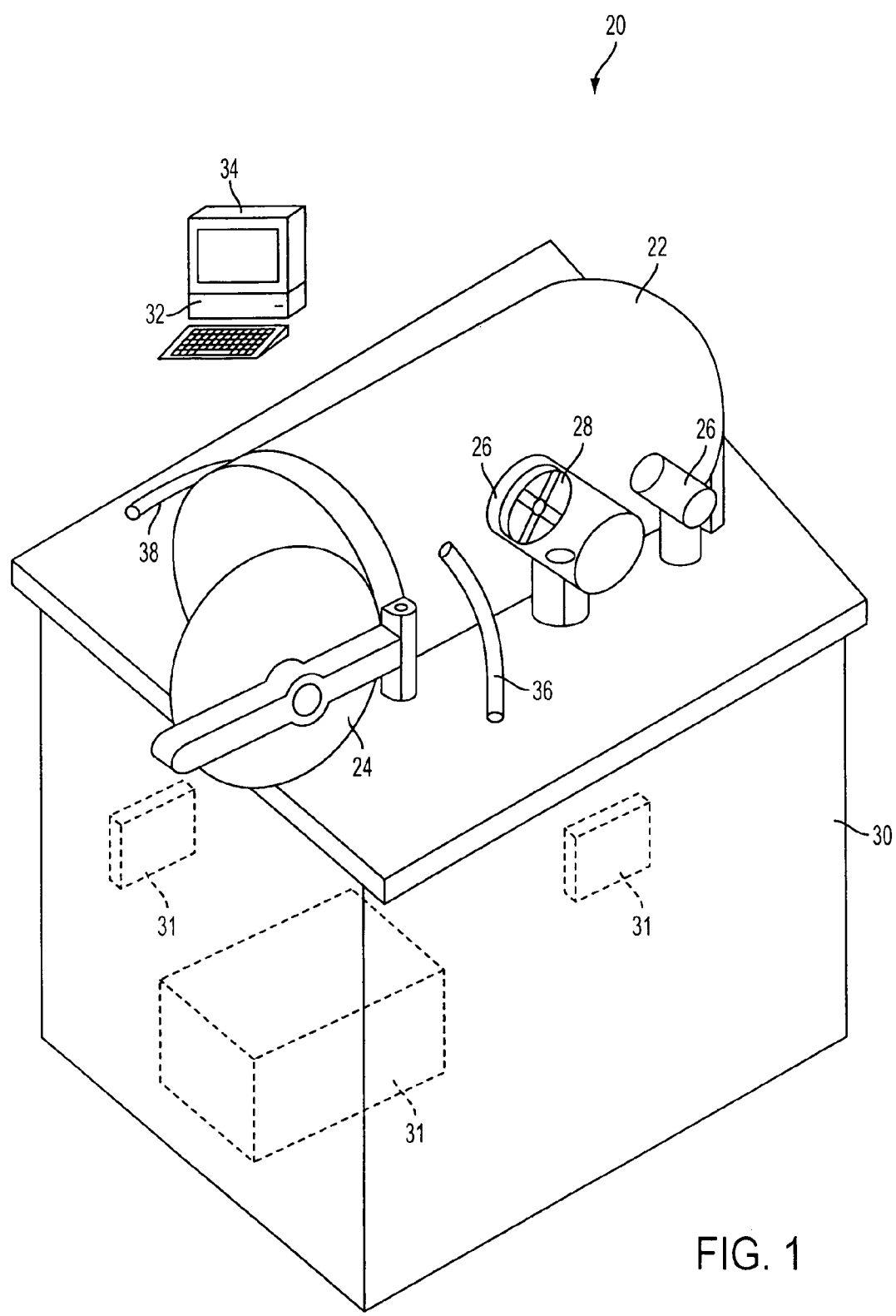
FIG. 1 is a representation of an infant sized plethysmographic chamber and air circulation system of the present invention.

Referring to FIG. 1, a representational view of the infant sized plethysmographic measurement chamber and air circulation system is shown. Plethysmographic system 20 is composed of plethysmographic measurement chamber 22, chamber door assembly 24, plethysmographic measurement components 26 (including volume perturbation element 28), and air circulation component chamber 30. Air circulation component chamber 30 houses air circulation components 31, which provide the mechanism for air circulation within chamber 22.

Plethysmographic measurement components 26 are coupled to computer 32, which includes software 34 for controlling the operation of plethysmographic measurement components 26.

Air circulation component chamber 30 is coupled to measurement chamber 22 via inlet tube 36 and exhaust tube 38. Inlet tube 36 and exhaust tube 38 allow for air to be continuously circulated and renewed within measurement chamber 22 through the operation of air circulation components 31. As described in more detail in connection with preferred embodiments of the invention, inlet tube 36 and exhaust tube 38 could comprise multiple parallel tubes in accordance with the present invention. Such an arrangement would result in quieter, laminar flow within the tubes, thereby generating less acoustic noise, at the expense of increased flow resistance.

Figure 2:
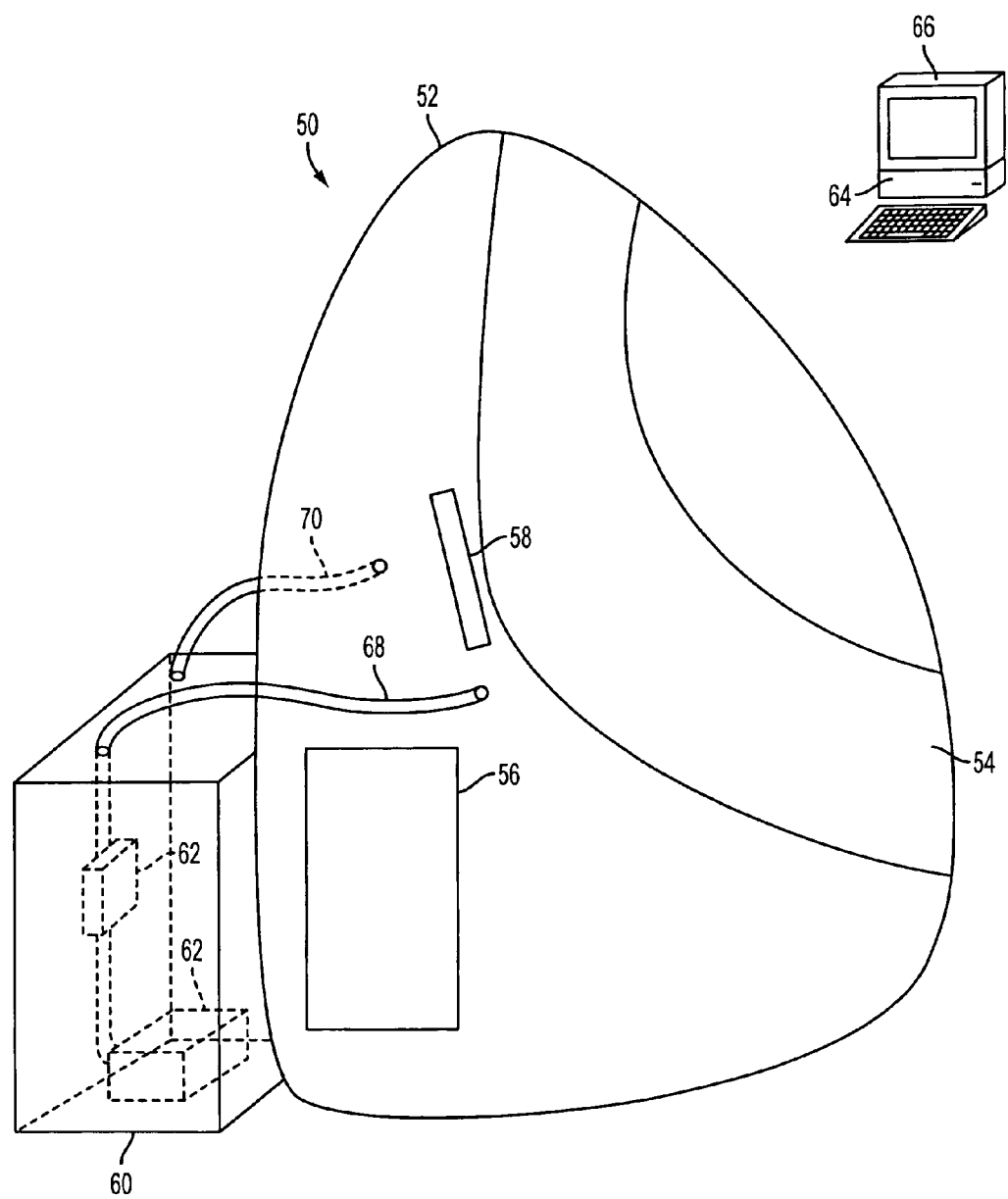
FIG. 2 is a representation of an adult sized plethysmographic chamber and air circulation system of the present invention.

Referring to FIG. 2, a representational view of an adult sized plethysmographic measurement chamber and air circulation system is shown. Plethysmographic system 50 is composed of plethysmographic measurement chamber 52, chamber door 54, plethysmographic measurement components 56 (including volume perturbation element 58), and air circulation component chamber 60, which houses air circulation components 62. Plethysmographic measurement components 56 are coupled to computer 64, which includes software 66 for controlling the operation of plethysmographic measurement components 56.

Air circulation component chamber 60 is coupled to measurement chamber 52 via inlet tube 68 and exhaust tube 70. Inlet tube 68 and exhaust tube 70 allow for air to be continuously renewed and circulated within measurement chamber 52 by air circulation components 62. As described in more detail in connection with preferred embodiments of the invention, inlet tube 68 and exhaust tube 70 could comprise multiple parallel tubes in accordance with the present invention.

One of ordinary skill in the art would understand that air circulation component chamber 60 could alternatively be housed within measurement chamber 52, so long as air circulation components 62 had access to ambient air outside of measurement chamber 52.

Measurement components 26, 56 may comprise volume perturbation element 29, 58 and means for determining pressure within the chamber, e.g., one or more pressure transducers. Volume perturbation element 28, 58 may generate pressure oscillations or volume perturbations within the measurement chamber at a perturbation frequency and may comprise, e.g., an oscillating diaphragm.

Figure 3:
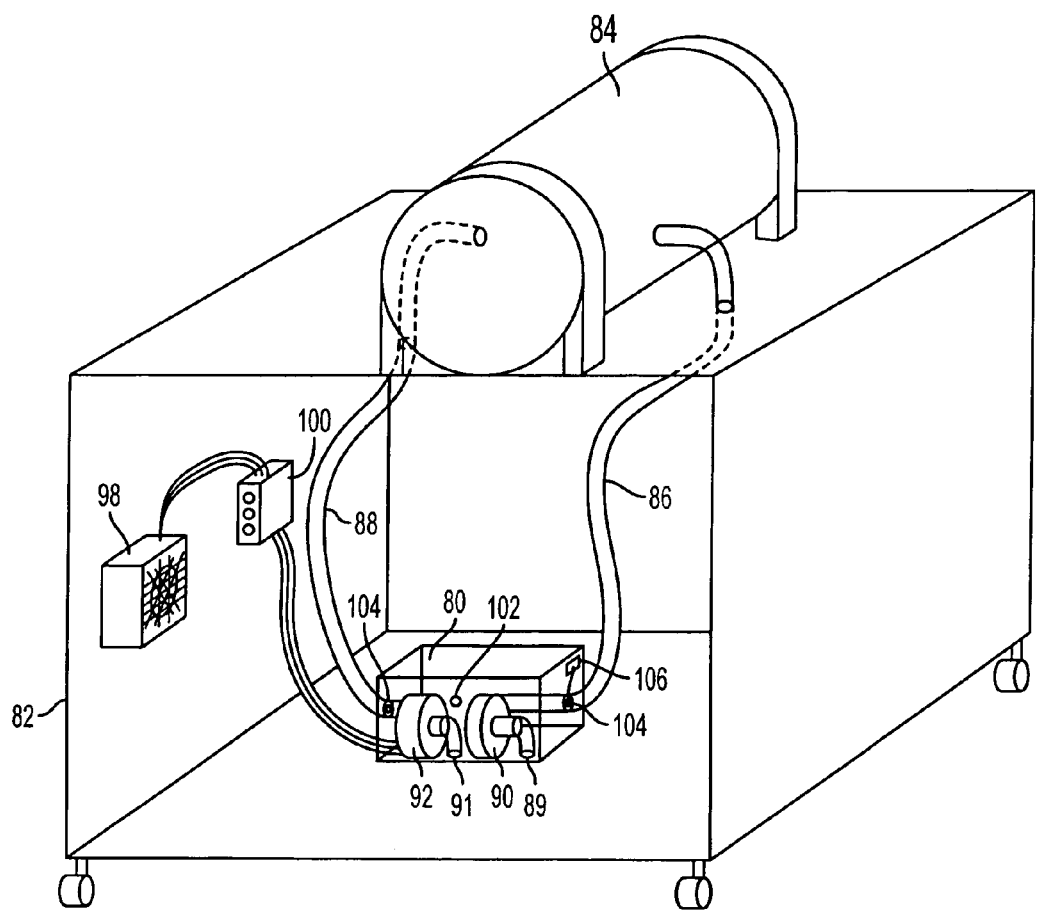
FIG. 3 is a detailed view of one embodiment the air circulation components of the present invention.

Referring now to FIG. 3, a view of one embodiment of the air circulation components of the present invention is described. Pump assembly 80 (shown housed within air circulation component chamber 82) is coupled to measurement chamber 84 via inlet tube 86 and exhaust tube 88. Pump assembly 80 both pumps ambient air through inlet tube 86 into measurement chamber 84, and pumps air contaminated with triatomic gasses (such as water vapor and $CO_2$) out of measurement chamber 84 through exhaust tube 88. Thus, air is continuously circulated and renewed within measurement chamber 84, preventing buildup of triatomic gasses that could affect the accuracy of plethysmographic measurement.

While in a preferred embodiment pump assembly 80 is housed within air circulation component chamber 82, one of ordinary skill in the art would recognize that pump assembly 80 could be physically located anywhere in relation to measurement chamber 84, so long as pump assembly 80 provided for circulation and renewal of air within chamber 84.

Pump assembly 80 is further comprised of one or more pumps for pumping air into and out of measurement chamber 84. In a preferred embodiment, pump assembly 80 further comprises inlet 89, inlet pump 90, exhaust 91 and exhaust pump 92. Inlet pump 90 pumps ambient air from inlet 89 through inlet tube 86 into measurement chamber 84, and exhaust pump 92 pumps contaminated air out of measurement chamber 84 through exhaust tube 88 and out exhaust 91.

Inlet pump 90 and exhaust pump 92 are preferably turbine or centrifugal pumps. However, one of ordinary skill in the art would recognize that other types of pumps suitable for pumping gasses could be used in accordance with the present invention, including fan pumps, diaphragm pumps, peristaltic pumps, and piston pumps.

Preferably, inlet pump 90 and exhaust pump 92 are placed at the ends of inlet tube 86 and exhaust tube 88 distal from measurement chamber 84, respectively. This placement allows for maximum attenuation of noise generated by inlet pump 90 and exhaust pump 92. However, inlet pump 90 and exhaust pump 92 may be placed at any point in the airflow between measurement chamber 84 and atmosphere in accordance with the present invention.

As one of ordinary skill in the art would understand, pump assembly 80 could also be comprised of a single pump, as opposed to a combination of input and exhaust pumps. While such a pump assembly would result in chamber pressure somewhat different from ambient, this may well be acceptable in some plethysmographic measurement systems. One of ordinary skill in the art would further recognize that inlet pump 90 and exhaust pump 92 do not have to be placed within a single pump assembly. For example, inlet pump 90 and exhaust pump 92 could be mounted separately within air circulation component chamber 82. Further, one or both of inlet pump 90 and exhaust pump 92 could be mounted outside of air circulation component chamber 82.

It is also preferable that inlet 89 and exhaust 91 be kept separate from one another. Such a placement of inlet 89 and exhaust 91 ensures that contaminated air pumped out of measurement chamber 84 is exhausted away from inlet 89, in order to prevent contamination of incoming air by excess $CO_2$ and water vapor being discharged from exhaust 91.

The physical properties of inlet tube 86 and exhaust tube 88 are important to maintain the acoustic properties of measurement chamber 84, such that accurate measurement of chamber volume can be attained in spite of the coupling of measurement chamber 84 to the external environment. More particularly, by coupling measurement chamber 84 to the environment, acoustic noise could pass through inlet tube 86 and exhaust tube 88 into measurement chamber 84, thereby affecting the accuracy of the body composition measurement. Further, acoustic energy at the frequency of perturbation could also leak outside measurement chamber 84, again affecting the accuracy of measurement.

However, the air within inlet tube 86 and exhaust tube 88 possesses inertia, which acts to resist movement of air within the tubes in response to pressure fluctuations (such as acoustic noise from outside measurement chamber 84, or the periodic perturbations generated during plethysmographic measurement). This property can be maximized through selection of the length of inlet tube 86 and exhaust tube 88.

As a first approximation, measurement chamber 84 and inlet tube 86 (or exhaust tube 88) can be modeled in a combined manner as a Helmholtz resonator. The Helmholtz resonator realized by the combination of measurement chamber 84 and inlet tube 86/exhaust tube 88 acts as a low-pass filter, attenuating acoustic noise above the resonant frequency of the system (which is inversely proportional to the square root of the length of the tube). Thus, the length of inlet tube 86 and exhaust tube 88 can be selected such that the acoustic low-pass filter properties of the chamber/tube system attenuate frequencies at or above the perturbation frequency. In a preferred embodiment of the invention, the lengths of the inlet tubes and exhaust tubes were selected such that the resonant frequency of the chamber/tube system was an order of magnitude below the perturbation frequency.

As a second approximation, the acoustic properties of inlet tube 86 and exhaust tube 88 can be looked at independently from measurement chamber 84. In so doing, the length of the tube would preferably be set at one-quarter the wavelength corresponding to the perturbation frequency in order to minimize transmission of pressure fluctuations through inlet tube 86 and exhaust tube 88 at the perturbation frequency. While adopting this model has been found to yield some benefit, in practice it has been found that simply ensuring that inlet tube 86 and exhaust tube 88 are of sufficient length to attenuate periodic signals at or above the frequency of perturbation (typically, between 3 Hz and 20 Hz, depending on the type of plethysmographic measurement system used) produces satisfactory results.

In a preferred embodiment, air circulation component chamber 82 further includes heater element 98, temperature monitoring circuitry 100, and controlled temperature inlet 102. In this embodiment, temperature monitoring circuitry 100 monitors the temperature of controlled temperature inlet 102, and varies the operation of heater element 98 to maintain a constant temperature within controlled temperature inlet 102. Controlled temperature inlet 102 acts as the source of air for inlet pump 90; thus, air is pumped from temperature controlled inlet 102 through inlet tube 86 into measurement chamber 84 by means of inlet pump 90. By providing for a controlled temperature environment within measurement chamber 84, the potential effects of temperature fluctuation in measurement chamber 84 due to body heat generated by the test subject are minimized.

Alternatively, heater element 98 can be used to heat the air within inlet tube 86 via conduction. In this embodiment, inlet pump 90 draws air through inlet 89 from the environment outside air circulation component chamber 82. Temperature monitoring circuitry 100 monitors the temperature of air within inlet tube 86, and varies the operation of heater element 98 to maintain a constant temperature of incoming air within inlet tube 86.

As another alternative, heater element 98 could be coupled to inlet pump 90, and used to directly heat the air within inlet tube 86.

It has also been found in practice that the flow rate of the air circulation system of the present invention can have an effect on the calibration of the plethysmographic measurement system. Systems and methods for calibrating plethysmographic measurement chambers are described in co-pending U.S. patent application Ser. No. 10/036,161, issued as U.S. Pat. No. 6,778,926, entitled "Calibration Methods and Apparatus for Plethysmographic Measurement Chambers," applied for by Philip Dempster, and filed on Dec. 31, 2001, which application is incorporated herein by reference in its entirety.

More particularly, as flow rate varies, dynamic resistance to pressure fluctuations also varies (under turbulent conditions). Stability of the system therefore can be improved by controlling flow rate. Thus, in a preferred embodiment, coupled to inlet tube 86 and/or exhaust tube 88 are one or more pressure transducers 104, which monitor the pressure drop across the inlet and/or exhaust tube. Pressure transducers 104 are further coupled to pump assembly 80 via feedback circuit 106. Feedback circuit 106, based on the input from pressure transducers 104, controls the operation of pump assembly 80 to provide for constant flow rate in the air circulation system. In a preferred embodiment, feedback circuit 106 varies the electrical power to pump assembly 80 to control flow rate.

One of ordinary skill in the art would recognize that other methods of maintaining flow rate may be used. For example, if pump assembly 80 comprises one or more rotary pumps, constant flow rate may be achieved by controlling the angular velocity of the rotary pump(s). One of ordinary skill in the art would also recognize that pressure drop may be measured across part or all of the tubing system comprised of inlet tube 86 and exhaust tube 88.

Further, while the particular flow rate selected must be sufficient to maintain acceptable levels of $CO_2$ and water vapor in measurement chamber 84, lower flow rates result in less acoustic noise being generated by the air circulation system. Thus, the particular flow rate selected should balance these two competing considerations. In practice, a wide range of flow rates were found to work successfully.

Figure 4:
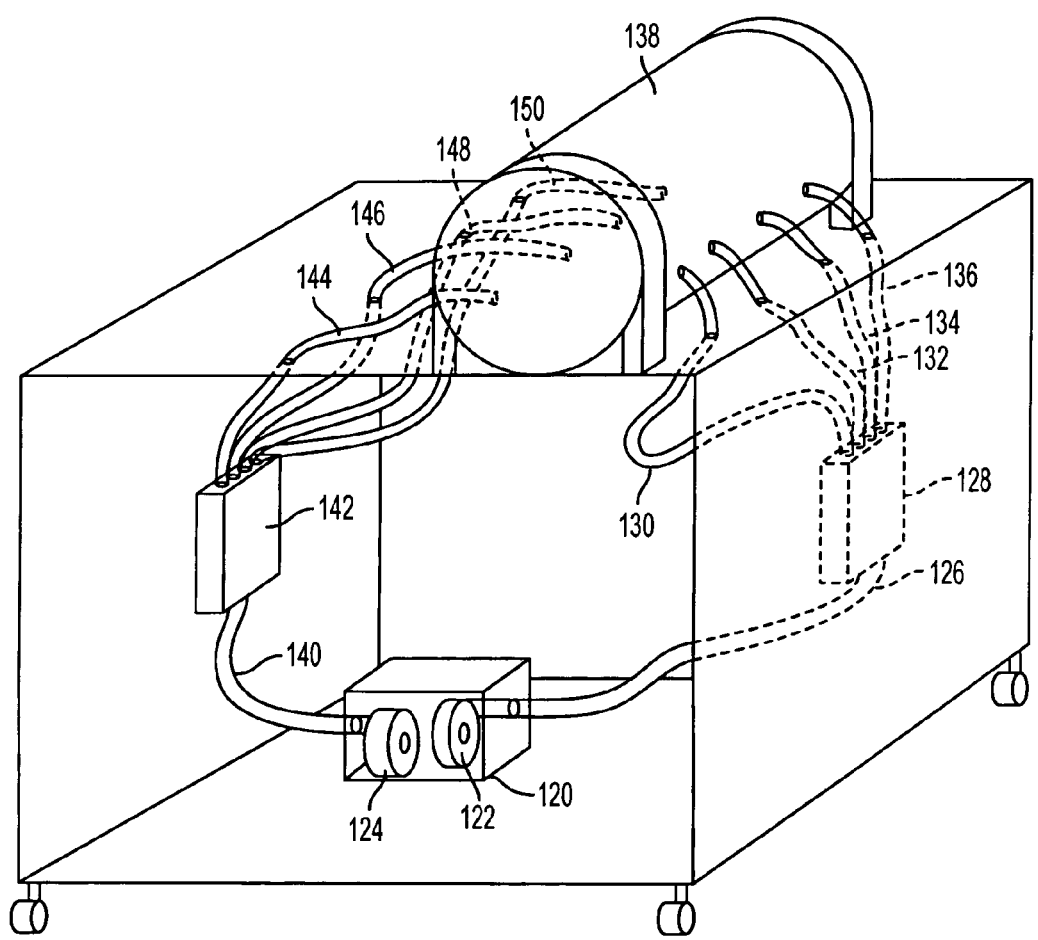
FIG. 4 is a detailed view of another embodiment of the air circulation components of the present invention.

Referring now to FIG. 4, a detailed view of a second embodiment of the air circulation components of the present invention is described. Pump assembly 120 includes inlet pump 122 and exhaust pump 124. Inlet pump 122 is coupled via inlet manifold tube 126 to inlet manifold 128. Inlet manifold 128 is coupled via parallel inlet chamber tubes 130, 132, 134, and 136 to measurement chamber 138. Similarly, exhaust pump 124 is coupled via exhaust fold tube 140 to exhaust manifold 142. Exhaust manifold 142 is coupled via parallel exhaust chamber tubes 144, 146, 148, and 150 to measurement chamber 138.

As with the previously described embodiments, pump assembly 120 both pumps ambient air through inlet manifold tube 126, inlet manifold 128, and inlet chamber tubes 130, 132, 134, and 136 into measurement chamber 138, and pumps air contaminated with triatomic gasses (such as water vapor and $CO_2$) out of measurement chamber 138 through exhaust chamber tubes 144, 146, 148, and 150, exhaust manifold 142, and exhaust manifold tube 140. By coupling both inlet manifold 128 and exhaust manifold 142 with measurement chamber 138 via multiple, parallel tubes, this embodiment both provides for reduced flow resistance in comparison to full lengths of multiple parallel tubes between the manifolds and measurement chamber 138, while at the same time providing quieter, laminar flow at the entry of measurement chamber 138 compared to the single inlet and exhaust tube embodiment described in connection with FIG. 3.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A plethysmographic measurement system, comprising:
   a plethysmographic measurement chamber;
   plethysmographic measurement components coupled to the measurement chamber, the measurement components comprising a volume perturbation element and means for determining pressure within the chamber; and
   an air circulation system coupled between the measurement chamber and an atmospheric environment outside the measurement chamber,
   wherein the air circulation system renews air within the measurement chamber using air from the atmospheric environment outside the chamber during plethysmographic measurement.

2. The system of claim 1, wherein the measurement components are housed within the measurement chamber.

3. The system of claim 1, further comprising a chamber door coupled to the measurement chamber.

4. The system of claim 1, wherein the means for determining pressure comprises one or more pressure transducers.

5. The system of claim 1, wherein the volume perturbation element is an oscillating diaphragm.

6. The system of claim 1, wherein the volume perturbation element generates pressure oscillations within the measurement chamber at a first frequency.

7. The system of claim 6, wherein the first frequency is between 3 and 20 Hz.

8. The system of claim 6, wherein the air circulation system comprises an inlet tube coupled between the measurement chamber and a pump assembly, and further comprises an exhaust tube coupled between the measurement chamber and pump assembly, wherein the inlet tube and exhaust tube attenuate noise at a perturbation frequency generated by the volume perturbation element.

9. The system of claim 8, wherein the length of the inlet tube is one quarter of a wavelength corresponding to the perturbation frequency.

10. The system of claim 8, wherein the length of the exhaust tube is one quarter of a wavelength corresponding to the perturbation frequency.

11. The system of claim 1, wherein the air circulation system comprises:
 a pump assembly;
 an inlet tube coupled between the measurement chamber and the pump assembly, and
 an exhaust tube coupled between the measurement chamber and pump assembly.

12. The system of claim 11, wherein the pump assembly comprises an inlet pump and an exhaust pump.

13. The system of claim 12, wherein the inlet pump is placed at the end of the inlet tube distal from the measurement chamber.

14. The system of claim 12, wherein the exhaust pump is placed at the end of the exhaust tube distal from the measurement chamber.

15. The system of claim 11, wherein the pump assembly comprises one or more rotary pumps.

16. The system of claim 11, wherein the pump assembly comprises one or more turbine pumps.

17. The system of claim 11, wherein the pump assembly comprises one or more centrifugal pumps.

18. The system of claim 11, wherein the pump assembly comprises one or more fan pumps.

19. The system of claim 11, wherein the pump assembly comprises one or more diaphragm pumps.

20. The system of claim 11, wherein the pump assembly comprises one or more piston pumps.

21. The system of claim 11, wherein the pump assembly comprises one or more peristaltic pumps.

22. The system of claim 11, further comprising: a plurality of parallel inlet tubes.

23. The system of claim 11, further comprising a plurality of parallel exhaust tubes.

24. The system of claim 11,
 wherein the means for determining pressure comprises a pressure transducer; and
 the system further comprises a feedback circuit coupled between the pump assembly and the pressure transducer, wherein the pressure transducer measures a flow rate of the air circulation system, and wherein the feedback circuit maintains a constant flow rate in the air circulation system.

25. The system of claim 24, wherein the pressure transducer is coupled to the inlet tube.

26. The system of claim 24 wherein the pressure transducer is coupled to the exhaust tube.

27. The system of claim 24, wherein the feedback circuit varies the operation of the pump assembly.

28. The system of claim 27, wherein the pump assembly comprises one or more rotary pumps, and wherein the feedback circuit varies the angular velocity of the one or more rotary pumps.

29. The system of claim 1, wherein the air circulation system comprises:
 a pump assembly;
 an inlet manifold;
 an inlet manifold tube coupled between the pump assembly and the inlet manifold;
 at least one inlet chamber tube coupled between the inlet manifold and the measurement chamber;
 an exhaust manifold;
 an exhaust manifold tube coupled between the exhaust manifold and the pump assembly; and
 at least one exhaust chamber tube coupled between the exhaust manifold and the measurement chamber.

30. The system of claim 29 wherein there are a plurality of parallel inlet chamber tubes coupled between the inlet manifold and the measurement chamber.

31. The system of claim 29 wherein there are a plurality of parallel exhaust chamber tubes coupled between the exhaust manifold and the measurement chamber.

32. The system of claim 1, wherein the volume perturbation element generates volume perturbations at a first perturbation frequency.

33. The system of claim 1, further comprising:
 a controlled temperature environment, wherein the air circulation system pumps air from the controlled temperature environment into the chamber.

34. The system of claim 33, wherein the air circulation system comprises:
 a pump assembly coupled to the controlled temperature environment;
 an inlet tube coupled between the measurement chamber and the pump assembly, and
 an exhaust tube coupled between the measurement chamber and pump assembly.

35. The system of claim 34, wherein the controlled temperature environment comprises;
 a heater element; and
 temperature monitoring circuitry coupled to the heater element.

36. The system of clam 35, wherein the temperature monitoring circuitry maintains a constant temperature within the controlled temperature environment.

37. The system of claim 36, wherein the temperature monitoring circuit controls the operation of the heater element.

38. The system of claim 1, further comprising:
 a pump assembly coupled to a controlled temperature inlet;
 an inlet tube coupled between the measurement chamber and the pump assembly;
 an exhaust tube coupled between the measurement chamber and the pump assembly; and
 temperature monitoring circuitry coupled to a heater element,
 wherein the temperature monitoring circuitry is configured to vary the operation of the heater element to maintain a constant temperature within the controlled temperature inlet.

39. A method of conducting plethysmographic measurement of a test subject, comprising:
 placing the subject to be measured in a plethysmographic measurement chamber,
 sealing said chamber;
 conducting plethysmographic measurement of the subject, and
 renewing air within the chamber using air from an atmospheric environment outside the chamber,
 wherein conducting plethysmographic measurement comprises:
  generating pressure oscillations within the chamber,
  measuring the amplitude of the pressure oscillations,
  calculating a volume of air within the chamber based on the measured pressure oscillations, and determining a body composition of the test subject based on the calculated volume of air within the chamber.

40. The method of claim 39, wherein generating pressure oscillations comprises:
oscillating a diaphragm at a fixed frequency.

41. The method of claim 39, wherein renewing air within the chamber comprises:
pumping air through an inlet tube into the chamber; and
pumping air through an exhaust tube out of the measurement chamber.

42. The method of claim 41, wherein pumping air through an inlet tube comprises:
establishing a controlled temperature environment; and
pumping air from the controlled temperature environment through the inlet tube.

43. The method of claim 42, wherein establishing a controlled temperature environment comprises:
measuring the temperature of an enclosed environment;
comparing the measured temperature to a desired control temperature;
varying the operation of a heater element in response to the comparison of the measured temperature to the desired temperature.

44. The method of claim 41 further comprising; heating the air with the inlet tube to a controlled temperature.

45. The method of claim 44, wherein heating the air with the inlet tube to a controlled temperature comprises:
measuring the temperature of air within the inlet tube;
comparing the measured temperature to a desired control temperature; and
varying the operation of a heater element in response to the comparison of the measured temperature to the desired temperature.

46. The method of claim 39, further comprising:
maintaining a constant flow rate of air being circulated through the chamber.

47. The method of claim 46, wherein maintaining a constant flow rate comprises:
measuring a flow rate;
comparing the measured flow rate to a desired flow rate, and
varying the operation of an air pump in response to comparing the measured flow rate to the control flow rate.

48. A plethysmographic measurement system, comprising:
a plethysmographic measurement chamber;
plethysmographic measurement components coupled to the measurement chamber; and
an air circulation system coupled between the measurement chamber and an atmospheric environment outside the measurement chamber,
wherein the air circulation system renews air within the measurement chamber using air from the atmospheric environment outside the chamber during plethysmographic measurement,
wherein the air circulation system comprises:
a pump assembly,
an inlet tube coupled between the measurement chamber and the pump assembly, and
an exhaust tube coupled between the measurement chamber and pump assembly.

49. A plethysmographic measurement system, comprising:
a plethysmographic measurement chamber;
plethysmographic measurement components coupled to the measurement chamber; and
an air circulation system coupled between the measurement chamber and an atmospheric environment outside the measurement chamber,
wherein the air circulation system renews air within the measurement chamber using air from the atmospheric environment outside the chamber during plethysmographic measurement,
wherein the air circulation system comprises:
a pump assembly,
an inlet manifold,
an inlet manifold tube coupled between the pump assembly and the inlet manifold,
at least one inlet chamber tube coupled between the inlet manifold and the measurement chamber,
an exhaust manifold,
an exhaust manifold tube coupled between the exhaust manifold and the pump assembly, and
at least one exhaust chamber tube coupled between the exhaust manifold and the measurement chamber.

50. A plethysmographic measurement system, comprising:
a plethysmographic measurement chamber;
plethysmographic measurement components coupled to the measurement chamber;
an air circulation system coupled between the measurement chamber and an atmospheric environment outside the measurement chamber, wherein the air circulation system renews air within the measurement chamber using air from the atmospheric environment outside the chamber during plethysmographic measurement; and
a controlled temperature environment, wherein the air circulation system pumps air from the controlled temperature environment into the chamber.

51. A method of conducting plethysmographic measurement of a test subject, comprising:
placing the subject to be measured in a plethysmographic measurement chamber,
sealing said chamber;
conducting plethysmographic measurement of the subject;
renewing air within the chamber using air from an atmospheric environment outside the chamber; and
maintaining a constant flow rate of air being circulated through the chamber.

* * * * *